US012751945B2

(12) United States Patent
Garcia-Ladona

(10) Patent No.: US 12,751,945 B2
(45) Date of Patent: Oct. 6, 2026

(54) COMPOUND FOR THE TREATMENT AND PREVENTION OF CENTRAL NERVOUS SYSTEM DISORDERS

(71) Applicant: ABAXYS THERAPEUTICS, Marbais (BE)

(72) Inventor: Francisco Javier Garcia-Ladona, Marbais (BE)

(73) Assignee: ABAXYS THERAPEUTICS, Marbais (BE)

( * ) Notice: Subject to any disclaimer, the term of this patent is extended or adjusted under 35 U.S.C. 154(b) by 911 days.

(21) Appl. No.: 17/789,876

(22) PCT Filed: Dec. 31, 2020

(86) PCT No.: PCT/EP2020/088071

§ 371 (c)(1),
(2) Date: Jun. 29, 2022

(87) PCT Pub. No.: WO2021/136827

PCT Pub. Date: Jul. 8, 2021

(65) Prior Publication Data

US 2023/0057133 A1 Feb. 23, 2023

Related U.S. Application Data

(60) Provisional application No. 62/955,502, filed on Dec. 31, 2019.

(51) Int. Cl.
*A61K 31/445* (2006.01)
*A61P 25/08* (2006.01)

(52) U.S. Cl.
CPC ............ *A61K 31/445* (2013.01); *A61P 25/08* (2018.01)

(58) Field of Classification Search
CPC ......... A61K 31/445; A61P 25/08; A61P 25/00
See application file for complete search history.

(56) References Cited

PUBLICATIONS

Xiaojiao et al. "Research progress on the relationship between ubiquitin carboxy terminal hydrolases L1 (UCH L1) and neuropsychiatric disorders" Journal of Psychiatry, vol. 27, No. 1, pp. 66-70.
International Search Report and Written Opinion issued on May 3, 2021, in connection with corresponding International Application No. PCT/EP2020/088071; 7 pages.
Mitsui et al., "Identification of a novel chemical potentiator and inhibitors of UCH-L1 by in silico drug screening"; Neurochemistry international; Apr. 1, 2010; vol. 56, No. 5, pp. 679-686.

*Primary Examiner* — Sahar Javanmard
(74) *Attorney, Agent, or Firm* — Maier & Maier, PLLC

(57) ABSTRACT

A pharmaceutical composition for use in the treatment and/or prevention of a central nervous system disorder, such as a motor disorder, a mood disorder, a neurological disorder, a neurodegenerative disorder, or an inflammatory disorder induced by a pathogenic factor or agent. The pharmaceutical composition includes a compound of formula (I):

(I)

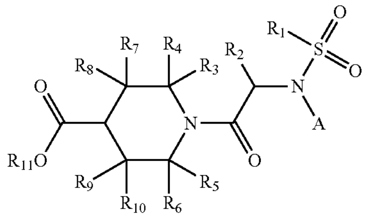

or any salt, derivative, isotope or mixture thereof, and at least one pharmaceutically acceptable excipient.

10 Claims, 8 Drawing Sheets

COMPOUND FOR THE TREATMENT AND PREVENTION OF CENTRAL NERVOUS SYSTEM DISORDERS

FIELD

The present invention relates to a pharmaceutical composition of 4-piperidinecarboxylate derivative. In particular, the present invention relates to a pharmaceutical composition comprising 4-piperidinecarboxylate derivative and at least one pharmaceutically acceptable excipient, for use in the treatment and/or prevention of brain disorders.

BACKGROUND

The human brain function is basically supported by the synaptic activity that is the result of neurotransmitter systems action in conjunction with that of other biological targets. The complex structural organization of the neurons and their neurotransmitter systems, in particular their presence in discrete anatomical areas, allows to function and control all basic activities in human body.

Brain diseases are the result of defective or significant loss of synaptic activity due to, yet, unknown or known factors including, but not limited to, developmental disturbances, genetic mutations on biological targets, tumours, toxic substances, neurodegenerative processes affecting brain structures, inflammatory processes, aging, or brain injuries due to traumatic events. The major consequences of brain diseases are a dysregulated function leading to hyperexcitation or a loss of activity of neurotransmission due to particular compensatory mechanisms.

Brain disorders and associated syndromes are mostly characterized of such synaptic activity imbalances. Epilepsy is characterized by a dysregulated excitatory and inhibitory activity of neurotransmitters systems leading to an uncontrolled focal, episodic and disabling excitatory hyperactivity. The origin of epilepsy could be due to genetic and non-genetic causes such as brain injuries and tumours. Parkinson's disease is characterized by the massive loss of dopaminergic system leading to an imbalance in the function of the several brain areas and neurotransmitters controlling motor function and thus producing severely disabling motor disturbances. Other neurological diseases have been associated to neurotransmitter disturbances such schizophrenia, psychotic disorders, attention deficits, obsessive compulsive disorders with an important contribution of significant dopaminergic hyperactivity, or Alzheimer's and cognitive impairment that have been suggested to be the result of wrong hyperactivity due to deficits generated by degenerative processes. Inflammatory processes caused by different factors such as toxic substances or viral infections could severely affect brain function and has been associated to participate or being a key factor in neurodegenerative diseases. Chronic inflammation can lead to tissue damage and ultimately its destruction, and often results from an inappropriate immune response. Inflammation in the nervous system ("neuroinflammation"), especially when prolonged, can be particularly injurious. While inflammation per se may not cause disease, it contributes importantly to disease pathogenesis across the central nervous system.

The consequences are devastating for patients' life and while several active agents have been identified and developed for the treatment of these brain diseases, such as L-DOPA or dopamine agonist treatment (for Parkinson's disease), GABA modulators and others (for epilepsy), these drugs have resulted either to be only partially efficacious, or fully inefficacious at least for an important part of the patients population, or are associated to important side effects, which in turn remain a major unsolved problem for patients.

In addition, many brain disorders and syndromes associated or not to major brain diseases remain intractable for now, such as multiple system atrophy, restless leg syndrome, dystonia, infantile epilepsy syndromes, neuromuscular disorders.

A huge unmet medical need exists for the treatment of human brain diseases. The present invention represents a new treatment for above mentioned disorders characterized by a pathological dysregulated synaptic activity or neurodegenerative processes.

SUMMARY

The present invention relates to a pharmaceutical composition for use in the treatment and/or prevention of a central nervous system disorder, comprising a compound of formula (I):

(I)

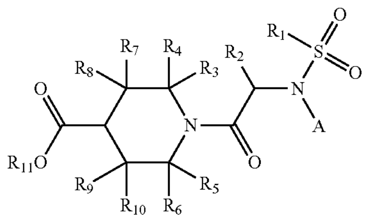

or a salt, derivative, isotope or mixture thereof, wherein $R_1$, $R_2$ and $R_{11}$ are each independently $C_1$-$C_3$ alkyl; $R_3$, $R_4$, $R_5$, $R_6$, $R_7$, $R_8$, $R_9$ and $R_{10}$ are each independently selected from hydrogen, halogen, hydroxyl, —$NH_3$, —$NO_3$, —SH, $C_1$-$C_3$ alkyl, $C_1$-$C_3$ haloalkyl, $C_1$-$C_3$ alkoxy and $C_1$-$C_3$ thioalkyl; and A is a 5- or 6-membered aromatic ring comprising 0, 1 or 2 nitrogen atoms, the 5- or 6-membered aromatic ring being not substituted or substituted by 1, 2, 3 or 4 groups, each group being independently selected from halogen, hydroxyl, —$NH_3$, —$NO_3$, —SH, $C_1$-$C_3$ alkyl, $C_1$-$C_3$ haloalkyl, $C_1$-$C_3$ alkoxy and $C_1$-$C_3$ thioalkyl, and at least one pharmaceutically acceptable excipient.

In one embodiment, A is selected from phenyl, pyridine, pyrrole, imidazole, pyrazole, diazine and triazine; preferably is phenyl.

In one embodiment, the compound of formula (I) is of formula (II):

(II)

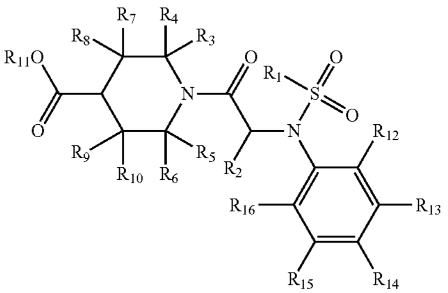

wherein $R_1$, $R_2$, $R_3$, $R_4$, $R_5$, $R_6$, $R_7$, $R_8$, $R_9$, $R_{10}$ and $R_{11}$ are as defined above in formula (I); $R_{12}$, $R_{13}$, $R_{15}$ and $R_{16}$ are each independently selected from hydrogen, halogen, hydroxyl, —$NH_3$, —$NO_3$, —SH, $C_1$-$C_3$ alkyl, $C_1$-$C_3$ haloalkyl, $C_1$-$C_3$ alkoxy and $C_1$-$C_3$ thioalkyl; and $R_{14}$ is $C_1$-$C_3$ alkyl.

In one embodiment, $R_1$ is a methyl group. In one embodiment, $R_2$ is a methyl group. In one embodiment, $R_{11}$ is an ethyl group. In one embodiment, $R_3$, $R_4$, $R_5$, $R_6$, $R_7$, $R_8$, $R_9$ and $R_{10}$ are each independently selected from hydrogen and $C_1$-$C_3$ alkyl, and preferably are hydrogen. In one embodiment, $R_{12}$, $R_{13}$, $R_{15}$ and $R_{16}$ are each independently selected from hydrogen and $C_1$-$C_3$ alkyl, preferably are hydrogen, and $R_{14}$ is $C_1$-$C_3$ alkyl, preferably is methyl.

In one embodiment, the central nervous system disorder is a motor disorder, a mood disorder, a neurological disorder, a neurodegenerative disorder, or an inflammatory disorder due to pathogenic factors or agents (neuroinflammation).

In one embodiment, the motor disorder is selected from Parkinson's disease, Huntington disease, muscular disorders, multiple system atrophy, genetic and non-genetic dystonia including functional dystonia, restless legs syndrome, cerebellar disorders, and medication-induced motor disorder. In one embodiment, the motor disorder is Parkinson's disease.

In one embodiment, the mood disorder is selected from psychotic disorders, schizophrenia, psychosis, bipolar disorder, bipolar depression, depression, anxiety, panic disorders, Tourette syndrome, obsessive compulsive disorders, and attention deficits disorders including attention deficit hyperactive disorders. In one embodiment, the mood disorder is anxiety.

In one embodiment, the neurological disorder is selected from Epilepsy, Alzheimer's Disease (AD), Mild Cognitive Impairment (MCI), Attention-Deficit Hyperactivity Disorder (ADHD), or Hyper-kinetic Disorder, agnosia, Amyotrophic Lateral Sclerosis (ALS), ataxia including Friedreich's ataxia, Canavan disease, dementia, neuralgia, migraine, headaches, tension headaches. In one embodiment, the neurological disorder is epilepsy.

In one embodiment, the neurodegenerative disorder is selected from Alzheimer's disease, Amyotrophic lateral sclerosis, Friedreich's ataxia, Huntington's disease, Lewy body disease, Parkinson's disease, Spinal muscular atrophy. In one embodiment, the neurodegenerative disorder is Alzheimer's disease.

In one embodiment, the inflammatory disorder due to pathogenic factors or agents is selected from encephalitis, myelitis, meningitis, grey matter atrophy, encephalopathy, HIV-induced neurological disorder, SARS-CoV-2-induced neurological disorder, neuronal destruction, infection or damage of oligodendrocytes, infection or damage of astrocytes, infection or damage of neurons, and apoptotic neurons. In one embodiment, the inflammatory disorder induced by a pathogenic factor or agent is selected from encephalitis, myelitis, meningitis, grey-matter atrophy, encephalopathy, HIV-induced neurological disorder, SARS-CoV-2-induced neurological disorder, and infection or damage of oligodendrocytes.

In one embodiment, the use of the invention further comprises administering another therapeutic agent for treating and/or preventing a central nervous system disorder. In one embodiment, the pharmaceutical composition further comprises another therapeutic agent for use in the treatment and/or prevention of a central nervous system disorder.

In one embodiment, the pharmaceutical composition is in an adapted form for an oral administration. In one embodiment, the pharmaceutical composition is in the form of a film.

DETAILED DESCRIPTION

Figure 1:
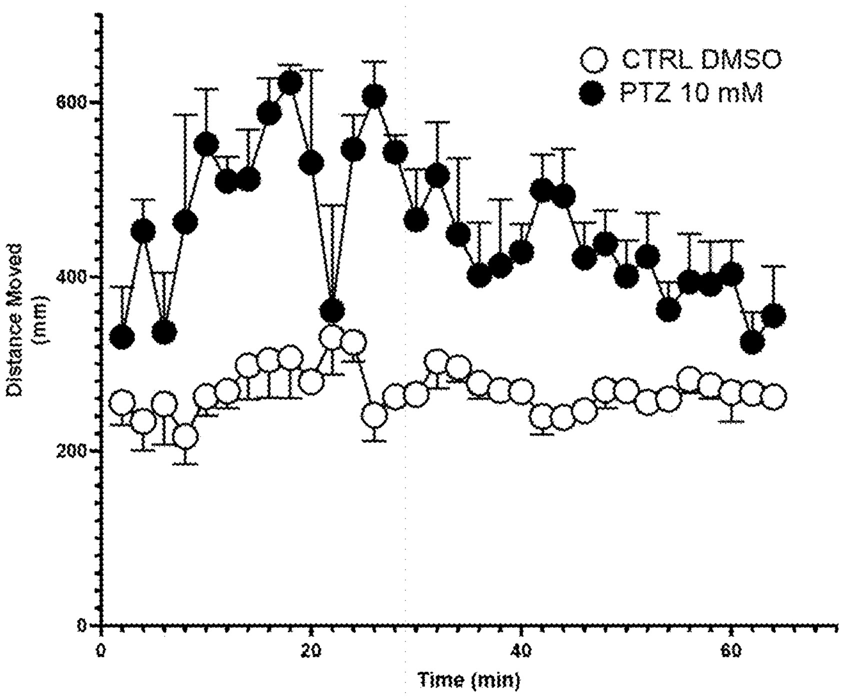
FIG. 1 is a graph showing distance moved by zebra fish larvae treated with a vehicle (CTRL, open circles), pentetrazole at a concentration of 10 mM (black circles)

In the present invention, the following terms have the following meanings:

"About" preceding a figure means plus or less 10% of the value of said figure.

"Alkoxy" refers to a group of formula —O-alkyl

"Alkyl" refers to any saturated linear or branched hydrocarbon chain with 1 to 12 carbon atoms; preferably 1 to 6 carbon atoms; more preferably 1 to 3 carbon atoms. Examples of alkyl groups are methyl, ethyl, n-propyl, i-propyl, n-butyl, i-butyl, s-butyl, t-butyl, pentyl and its isomers (e.g. n-pentyl or i-pentyl), or hexyl and its isomers (e.g., n-hexyl or i-hexyl). Preferably, alkyl is ethyl or methyl; more preferably methyl.

"Aryl" refers to a polyunsaturated, aromatic hydrocarbon group comprising from 5 to 12 carbon atoms, preferably 6 to 10 carbon atoms, more preferably 5 or 6 carbon atoms, having a single ring (i.e., phenyl) or multiple aromatic rings fused together (e.g., naphtyl) or linked covalently, wherein at least one ring is aromatic. The aromatic ring may optionally include one to two additional rings (either cycloalkyl, heterocyclyl or heteroaryl) fused thereto. Examples of aryl are phenyl, biphenylyl, biphenylenyl, 5- or 6-tetralinyl, naphthalen-1- or -2-yl, 4-, 5-, 6 or 7-indenyl, 1-2-, 3-, 4- or 5-acenaphtylenyl, 3-, 4- or 5-acenaphtenyl, 1- or 2-pentalenyl, 4- or 5-indanyl, 5-, 6-, 7- or 8-tetrahydronaphthyl, 1,2,3,4-tetrahydronaphthyl, 1,4-dihydronaphthyl, 1-, 2-, 3-, 4- or 5-pyrenyl.

"Aromatic ring" refers collectively to aryl and heteroaryl groups.

"Haloalkyl" refers to an alkyl group as defined hereinabove, wherein at least one hydrogen atom has been replaced by a halogen atom selected from fluoride, chloride, bromide and iodine. Preferably, each halogen atom in the haloalkyl is fluoride, i.e., the haloalkyl is a "fluoroalkyl".

"Heteroaryl" refers to an aromatic rings or aromatic ring systems comprising from 5 to 12 carbon atoms, preferably 6 to 10 carbon atoms, more preferably 4 or 5 carbon atoms, having one or two rings which are fused together or linked covalently, wherein at least one ring is aromatic, and wherein one or more carbon atoms in one or more of these rings is replaced by oxygen, nitrogen and/or sulfur atoms, wherein the nitrogen and sulfur heteroatoms may optionally be oxidized and the nitrogen heteroatoms may optionally be quaternized. Such rings may be fused to an aryl, cycloalkyl, heteroaryl or heterocyclyl ring. Examples of heteroaryl are furanyl, thiophenyl, pyrazolyl, imidazolyl, oxazolyl, isoxazolyl, thiazolyl, isothiazolyl, triazolyl, oxadiazolyl, thiadiazolyl, tetrazolyl, oxatriazolyl, thiatriazolyl, pyridinyl, pyrimidyl, pyrazinyl, pyridazinyl, oxazinyl, dioxinyl, thiazinyl, triazinyl, imidazo[2, 1-b] [1,3] thiazolyl or thieno [3,2-b] furanyl.

"Pharmaceutically acceptable" used in conjunction with an ingredient of a composition, it is meant that the ingredients of a pharmaceutical composition are compatible with each other and not deleterious to the subject to which the pharmaceutical composition is administered.

"Pharmaceutically acceptable excipient" refers to an excipient or vehicle that does not produce an adverse, allergic or other untoward reaction when administered to a subject, preferably a human. It includes any and all solvents, dispersion media, coatings, antibacterial and antifungal agents, isotonic and absorption delaying agents, and the like. For human administration, preparations should meet sterility, pyrogenicity, general safety and purity standards as required by regulatory offices, such as Food and Drug Administration (FDA) office or European Medicine Agency (EMA).

"Pharmaceutical composition" refers to a composition comprising at least a pharmaceutically active agent in association with at least a pharmaceutically acceptable excipient. A pharmaceutical composition is for therapeutic use, and relates to health. Especially, a pharmaceutical composition may be indicated for treating a disease selected from eating disorders, e.g., obesity.

"Solvate" refers to a molecular complex comprising a compound of the invention and stoichiometric or sub-stoichiometric amounts of one or more pharmaceutically acceptable solvent molecule such as ethanol. The term "hydrate" refers to when the solvent is water.

"Subject" refers to a warm-blooded animal, preferably a mammal, more preferably a human. Preferably, the subject is a patient, i.e., a subject who is awaiting the receipt of, or who is receiving medical care, or who is/will be the object of a medical procedure. For example, a subject may be treated for eating disorders, e.g., obesity.

"Thioalkyl" refers to a group of formula —S-alkyl.

"Therapeutic agent", "active agent" and "pharmaceutically active agent" are synonyms and refer to a compound for therapeutic use, and relates to health. Especially, a therapeutic agent may be indicated for treating eating disorders, e.g., obesity.

"Treating" or "treatment" or "alleviation" refers to both therapeutic treatment and prophylactic or preventative measures; wherein the object is to prevent or slow down (lessen) the targeted disease or condition in a subject in need thereof. Those in need of treatment include those already with the disease or condition as well as those prone to have the disorder or those in whom the disorder is to be prevented. A subject is successfully "treated" for a disease or pathological factor if, after receiving a therapeutic amount of an compound or composition according to the present invention, the subject shows observable and/or measurable reduction in or absence of one or more of the following: reduction in the number of pathogenic cells; reduction in the percent of total cells that are pathogenic; relief to some extent, of one or more of the symptoms associated with the specific disease or condition; reduced morbidity and mortality; and/or improvement in quality of life issues. The above parameters for assessing successful treatment and improvement in the disease are readily measurable by routine procedures familiar to a physician. For example, the disease may be selected from eating disorders, e.g., obesity.

The term "individual" refers to a vertebrate animal, preferably a mammal, more preferably a human. Examples of individuals include humans, non-human primates, dogs, cats, mice, rats, horses, cows, sheep and transgenic species thereof. In one embodiment, an individual may be a "patient", i.e. a warm-blooded animal, more preferably a human, who/which is awaiting the receipt of, or is receiving medical care or was/is/will be the object of a medical procedure, or is monitored for the development of a disease. In one embodiment, the individual is an adult (for example a human subject above the age of 18). In another embodiment, the individual is a child (for example a human subject below the age of 18). In one embodiment, the individual is a male. In another embodiment, the individual is a female.

The invention relates to a pharmaceutical composition comprising a compound of formula (I):

(I)

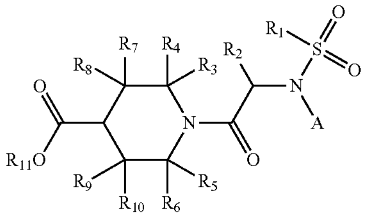

or a salt, derivative, isotope or mixture thereof, wherein:

$R_1$, $R_2$ and $R_{11}$ are each independently $C_1$-$C_3$ alkyl, $R_3$, $R_4$, $R_5$, $R_6$, $R_7$, $R_8$, $R_9$ and $R_{10}$ are each independently selected from hydrogen, halogen, hydroxyl, —$NH_3$, —$NO_3$, —SH, $C_1$-$C_3$ alkyl, $C_1$-$C_3$ haloalkyl, $C_1$-$C_3$ alkoxy and $C_1$-$C_3$ thioalkyl, and A is a 5- or 6-membered aromatic ring comprising 0, 1 or 2 nitrogen atoms, the 5- or 6-membered aromatic ring being not substituted (i.e., unsubstituted) or substituted by 1, 2, 3 or 4 groups, each group being independently selected from halogen, hydroxyl, —$NH_3$, —$NO_3$, —SH, $C_1$-$C_3$ alkyl, $C_1$-$C_3$ haloalkyl, $C_1$-$C_3$ alkoxy and $C_1$-$C_3$ thioalkyl, and at least one pharmaceutically acceptable excipient.

As it comprises a piperidine moiety substituted on position 4 by a carboxylate group ($COOR_{11}$), the compound of formula (I) hereinabove qualifies as a "4-piperidinecarboxylate derivative" in the sense of the present invention.

In one embodiment, A is a 5- or 6-membered aromatic ring selected from phenyl, pyridine, pyrrole, imidazole, pyrazole, diazine (i.e., pyrazine, pyrimidine or pyridazine) and triazine, the 5- or 6-membered aromatic ring being not substituted or substituted as defined above under formula (I). In one embodiment, A is phenyl, the phenyl being not substituted or substituted as defined above under formula (I). In one embodiment, A is a 4-alkylphenyl, i.e., a phenyl at least substituted on position 4 by an alkyl group (such as for example a $C_1$-$C_3$ alkyl group).

In one embodiment, the compound of formula (I) is of formula (II):

(II)

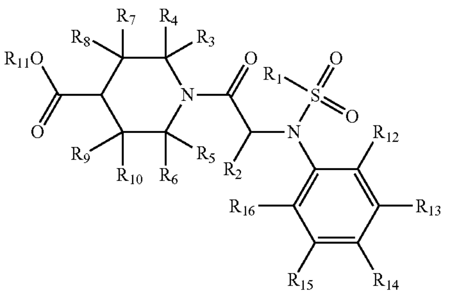

wherein:

$R_1$, $R_2$, $R_3$, $R_4$, $R_5$, $R_6$, $R_7$, $R_8$, $R_9$, $R_{10}$ and $R_{11}$ are as defined above in formula (I), $R_{12}$, $R_{13}$, $R_{15}$ and $R_{16}$ are each independently selected from hydrogen, halogen, hydroxyl, —$NH_3$, —$NO_3$, —SH, $C_1$-$C_3$ alkyl, $C_1$-$C_3$ haloalkyl, $C_1$-$C_3$ alkoxy and $C_1$-$C_3$ thioalkyl, and $R_{14}$ is $C_1$-$C_3$ alkyl.

In one embodiment, $R_1$ is selected from methyl, ethyl and propyl. In one embodiment, $R_1$ is a methyl group.

In one embodiment, $R_2$ is selected from methyl, ethyl and propyl. In one embodiment, $R_2$ is a methyl group.

In one embodiment, $R_{11}$ is selected from methyl, ethyl and propyl. In one embodiment, $R_{11}$ is an ethyl group.

In one embodiment, $R_3$, $R_4$, $R_5$, $R_6$, $R_7$, $R_8$, $R_9$ and $R_{10}$ are each independently selected from hydrogen and $C_1$-$C_3$ alkyl. In one embodiment, $R_4$, $R_6$, $R_8$ and $R_{10}$ are hydrogen. In one embodiment, $R_3$, $R_4$, $R_5$, $R_6$, $R_7$, $R_8$, $R_9$ and $R_{10}$ are hydrogen.

In one embodiment, $R_{12}$, $R_{13}$, $R_{15}$ and $R_{16}$ are each independently selected from $C_1$-$C_3$ alkyl, $C_1$-$C_3$ haloalkyl, $C_1$-$C_3$ alkoxy and $C_1$-$C_3$ thioalkyl. In one embodiment, $R_{12}$, $R_{13}$, $R_{15}$ and $R_{16}$ are each independently selected from hydrogen and $C_1$-$C_3$ alkyl. In one embodiment, $R_{12}$, $R_{13}$, $R_{15}$ and $R_{16}$ are hydrogen.

In one embodiment, $R_{14}$ is $C_1$-$C_3$ alkyl. In one embodiment, $R_{14}$ is selected from methyl, ethyl and propyl. In one embodiment, $R_{14}$ is a methyl group.

In one preferred embodiment, the compound of formula (I) is ethyl 1-(N-(methylsulfonyl)-N-(p-tolyl)alanyl)piperidine-4-carboxylate of formula (1) (hereafter "Compound 1" or "Cmpd1"):

(1)

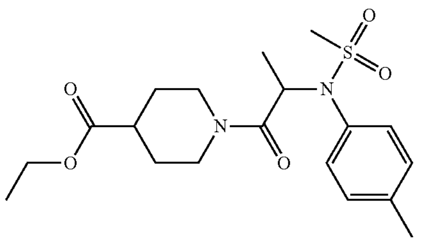

Compound 1 was named using ChemDraw® Professional 15.0 (PerkinElmer).

According to one embodiment, the at least one pharmaceutically acceptable excipient is clear to the skilled person; reference is made to the latest edition of Remington's Pharmaceutical Sciences.

Especially, the pharmaceutical composition of the invention can optionally contain such inactive substances that are commonly used in pharmaceutical formulations, such as for example cosolvents, lipid carrier, antioxidants, surfactants, wetting agents, emulsifying agents, buffering agents, pH modifying agents, preserving agents (or preservating agents), isotonifiers, stabilizing agents, granulating agents or binders, precipitation inhibitors, lubricants, disintegrants, glidants, diluents or fillers, adsorbents, dispersing agents, suspending agents, bulking agents, release agents, sweetening agents, flavoring agents, and the like.

In a preferred embodiment, the pharmaceutical composition of the invention comprises one or more pharmaceutically acceptable cosolvent. Preferably cosolvents are selected from caprylic acid, polyethylene glycol (PEG), propylene glycol, ethanol, dimethylsulfoxide, dimethylacetamide, dimethylisosorbide and mixtures thereof. In a specific embodiment, the pharmaceutical composition of the invention comprises caprylic acid and/or PEG. Advantageously, when the composition comprises PEG as cosolvent, PEG is of low molecular weight, preferably PEG is PEG 400. In an alternative embodiment, when the composition comprises PEG, it is of a moderate molecular weight, preferably PEG 3350.

In a specific embodiment, the pharmaceutical composition of the invention comprises one or more pharmaceutically acceptable lipid carrier. In a preferred embodiment, the lipid carrier is lauroyl polyoxyl-32 glycerides. This excipient corresponds to Gelucire® 44/14 manufactured by Gattefossé (Saint-Priest—France). This excipient is also known under the following references: lauroyl polyoxyl-32 glycerides NF/USP (NF: National Formulary; USP: US Pharmacopeia); lauroyl macrogol-32 glycerides EP (European Pharmacopeia); hydrogenated coconut PEG-32 esters (INCI); CAS number 57107-95-6. Gelucire® 44/14 corresponds to a well-defined multi-constituent substance constituted of mono-, di- and triglycerides and PEG-32 mono- and diesters of lauric acid (C12). Gelucire® 44/14 has a melting point ranging from 42.5° C. to 47.5° C. (with a mean at 44° C.) and a hydrophilic/lipophilic balance (HLB) value of 14.

In another embodiment, the lipid carrier is Vitamin E TPGS. This excipient is also known under the following references: D-α-Tocopherol polyethylene glycol-1000 succinate; Tocophersolan; Tocofersolan; VEGS; α-[4-[[(2R)-3,4-dihydro-2,5,7,8-tetramethyl-2-[(4R,8R)-4,8,12-trimethyltridecyl]-2H-1-benzopyran-6-yl]oxy]-1,4-dioxobutyl]-ω-hydroxy-poly(oxy-1,2-ethanediyl); Vitamin E PEG succinate and is formed from Vitamin E which is conjugated to polyethylene glycol 1000 via a succinic acid linker. Vitamin E TPGS has melting point in the range 37-41° C. and a hydrophilic/lipophilic balance (HLB) value of 13.

In one embodiment, the pharmaceutical composition of the invention comprises one or more antioxidant; preferably the antioxidant is selected from butylated hydroxytoluene (BHT), butylated hydroxyanisole (BHA), citric acid, sodium metabisulfite, ascorbic acid, methionine and vitamin E; more preferably the antioxidant is BHT.

In some embodiments, surfactants are added, such as for example polyethylene glycols, polyoxyethylene sorbitan fatty acid esters, sorbitan esters, sodium docusate, sodium lauryl sulfate, polysorbates (20, 80, etc.), poloxamers (188, 407 etc.), pluronic polyols, polyoxyethylene sorbitan monoethers (TWEEN®-20, TWEEN®-80, etc.), vitamin E TPGS (Vitamin E polyethylene glycol succinate), cremophor RH40 (polyoxyl 40 hydrogenated castor oil), cremophor EL (polyoxyl 35 hydrogenated castor oil), polyethylene glycol 660 12-monostearate, solutol HS15 (Polyoxyethylated 12-hydroxystearic acid), labrasol (caprylocaproyl polyoxyl-8 glycerides), labrafil M1944 (Oleoyl polyoxyl-6 glycerides), polylactide polyethylene glycol copolymer, polyvinyl caprolactam-polyvinyl acetate-polyethylene glycol graft copolymer (Soluplus®).

In some embodiments, wetting agents are added, such as for example sodium lauryl sulphate, vitamin E TPGS, sodium docusate, polysorbate 80, poloxamer 407. A preferred wetting agent is poloxamer 407.

In some embodiments, emulsifying agents are added, such as for example carbomer, carrageenan, lanolin, lecithin, mineral oil, oleic acid, oleyl alcohol, pectin, poloxamer, polyoxyethylene sorbitan fatty acid esters, sorbitan esters, triethanolamine, propylene glycol monolaurate, propylene glycol dilaurate, propylene glycol monocaprylate. Preferred emulsifying agents are for example poloxamer, propylene glycol monolaurate, propylene glycol dilaurate, and propylene glycol monocaprylate.

In some embodiments, buffering agents are used to help to maintain the pH in the range that approximates physiological conditions Suitable buffering agents include both organic and inorganic acids and salts thereof, such as citrate buffers (e.g., monosodium citrate-disodium citrate mixture, citric acid-trisodium citrate mixture, citric acid-monosodium citrate mixture, etc.), succinate buffers (e.g., succinic acid-monosodium succinate mixture, succinic acid-sodium hydroxide mixture, succinic acid-disodium succinate mixture, etc.), tartrate buffers (e.g., tartaric acid-sodium tartrate mixture, tartaric acid-potassium tartrate mixture, tartaric acid-sodium hydroxide mixture, etc.), fumarate buffers (e.g., fumaric acid-monosodium fumarate mixture, fumaric acid-disodium fumarate mixture, monosodium fumarate-disodium fumarate mixture, etc.), gluconate buffers (e.g., gluconic acid-sodium glyconate mixture, gluconic acid-sodium hydroxide mixture, gluconic acid-potassium glyuconate mixture, etc.), oxalate buffer (e.g., oxalic acid-sodium oxalate mixture, oxalic acid-sodium hydroxide mixture, oxalic acid-potassium oxalate mixture, etc.), lactate buffers (e.g., lactic acid-sodium lactate mixture, lactic acid-sodium hydroxide mixture, lactic acid-potassium lactate mixture, etc.) and acetate buffers (e.g., acetic acid-sodium acetate mixture, acetic acid-sodium hydroxide mixture, etc.). Additionally, phosphate buffers, histidine buffers and trimethylamine salts such as Tris can be used.

In some embodiments, pH modifiers are added, such as for example sodium hydroxide, sodium bicarbonate, magnesium oxide, potassium hydroxide, meglumine, sodium carbonate, citric acid, tartaric acid, ascorbic acid, fumaric acid, succinic acid and malic acid.

In some embodiments, preservatives agents are added to retard microbial growth. Suitable preservatives for use with the present disclosure include phenol, benzyl alcohol, meta-cresol, methyl paraben, propyl paraben, octadecyldimethylbenzyl ammonium chloride, benzalconium halides (e.g., chloride, bromide, and iodide), hexamethonium chloride, and alkyl parabens such as methyl or propyl paraben, catechol, resorcinol, cyclohexanol, and 3-pentanol.

In some embodiments, isotonifiers sometimes known as "stabilizers" are added and include polyhydric sugar alcohols, for example trihydric or higher sugar alcohols, such as glycerin, erythritol, arabitol, xylitol, sorbitol and mannitol. Stabilizers refer to a broad category of excipients which can range in function from a bulking agent to an additive which solubilizes the therapeutic agent or helps to prevent denaturation or adherence to the container wall or helps to inhibit the precipitation, particle growth or agglomeration of the active ingredient. Typical stabilizers can be polyhydric sugar alcohols (enumerated above); amino acids such as arginine, lysine, glycine, glutamine, asparagine, histidine, alanine, ornithine, L-leucine, 2-phenylalanine, glutamic acid, threonine, etc.; organic sugars or sugar alcohols, such as lactose, trehalose, stachyose, mannitol, sorbitol, xylitol, ribitol, myoinisitol, galactitol, glycerol and the like, including cyclitols such as inositol; polyethylene glycol; amino acid polymers; sulfur containing reducing agents, such as urea, glutathione, thioctic acid, sodium thioglycolate, thioglycerol, α-monothioglycerol and sodium thio sulfate; low molecular weight polypeptides (e.g., peptides of 10 residues or fewer); proteins such as human serum albumin, bovine serum albumin, gelatin or immunoglobulins; hydrophylic polymers, such as polyvinylpyrrolidone; poloxamer 407; cellulose derivatives such as hydroxypropylmethylcellulose, hydroxypropylmethylcellulose phthalate or hydroxypropylmethylcellulose acetate succinate; carboxymethylcellulose (Na/Ca); monosaccharides, such as xylose, mannose, fructose, glucose; disaccharides such as lactose, maltose, sucrose and trisaccharides such as raffinose; polysaccharides such as dextran; polyethylene glycol methyl ether-block-poly(D-L-lactide) copolymer; poly(butyl methacrylate-co-(2-dimethylaminoethyl) methacrylate-co-methyl methacrylate) 1:2:1. Preferred stabilizers are for example glycerol; polyethylene glycol; polyvinylpyrrolidone; cellulose derivatives such as hydroxypropylmethylcellulose, hydroxypropylmethylcellulose phthalate or hydroxypropylmethylcellulose acetate succinate; carboxymethylcellulose (Na/Ca); polyethylene glycol methyl ether-block-poly(D-L-lactide) copolymer; and poly(butyl methacrylate-co-(2-dimethylaminoethyl) methacrylate-co-methyl methacrylate) 1:2:1, polyvinyl caprolactam-polyvinyl acetate-polyethylene glycol graft copolymer, polyvinylpyrrolidone polyvinylacetate copolymer.

In some embodiments, granulating agent/binder(s) are added, such as for example starch, gums (inclusive of natural, semisynthetic and synthetic), microcrystalline cellulose, ethyl cellulose, methylcellulose, hydroxypropylcellulose, polymers such as povidone, polyvinylpyrrolidone polyvinylacetate copolymer and the like. Preferred granulating agents are for example methylcellulose, hydroxypropylcellulose, povidone and polyvinylpyrrolidone polyvinylacetate copolymer.

In some embodiments, precipitation inhibitors are added, such as for example water soluble derivatives of cellulose including hydroxypropylmethylcellulose and methylcellulose, and water-soluble polymers such as polyvinylpyrrolidone, polyvinylpyrrolidone polyvinylacetate copolymer, polyvinyl caprolactam-polyvinyl acetate-polyethylene glycol graft copolymer or poloxamer 407. A preferred precipitation inhibitor is hydroxypropylmethylcellulose.

In some embodiments, lubricants are added, such as for example magnesium stearate, glyceryl esters, behenoyl polyoxyl-8 glycerides Nf (Compritol HD5 ATO), sodium stearyl fumarate and the like.

In some embodiments disintegrants are added, such as for example synthetics like sodium starch glycolate, cross povidone, cross carmellose sodium, kollidon CL, and natural origin such as locust bean gum and the like.

In some embodiments glidants are added, such as for example talc, magnesium stearate, colloidal silicon dioxide, starch and the like.

In some embodiments, diluents (or fillers) are added, such as for example dextrose, lactose, mannitol, microcrystalline cellulose, sorbitol, sucrose, dibasic calcium phosphate, calcium sulphate dehydrate, starch and the like.

In some embodiments, adsorbents are added, such as for example silicon dioxide, purified aluminium silicate and the like.

In some embodiments, the pharmaceutical composition comprising the combination of the invention is in the form of tablets and tableting excipients are added, such as for example granulating agents, binders, lubricants, disintegrants, glidants, diluents, adsorbents and the like.

In some embodiments the pharmaceutical composition of the invention is in the form of capsules, in which the capsule shells are constructed from gelatin or from non-animal derived products such as cellulose and its derivatives such as hydroxypropylmethylcellulose. Other ingredients may be included in the capsule shells such as polyethyleneglycol to act as plasticizer; pigments such as titanium dioxide or iron oxide to provide opacity and colour differentiation; lubricants such as carnauba wax; gelling agents such as carrageenan and wetting agents such as sodium lauryl sulphate. In one embodiment, the pharmaceutical composition of the invention is formulated as capsules, wherein the capsule shells are constructed from gelatin and wherein additional components are optionally included in the capsule shells, such as for example polyethylene glycol and sodium lauryl sulphate.

By means of non-limiting examples, the pharmaceutical composition of the invention may be in a form suitable for oral administration, for parenteral administration (such as by intravenous, intramuscular or subcutaneous injection or intravenous infusion), for topical administration (including ocular), for rectal administration, for administration by inhalation, by a skin patch, by an implant, by a suppository, etc. Such suitable administration forms—which may be solid, semi-solid or liquid, depending on the manner of administration—as well as methods and carriers, diluents and excipients for use in the preparation thereof, will be clear to the skilled person; reference is made to the latest edition of Remington's Pharmaceutical Sciences.

The compositions may be formulated so as to provide rapid, sustained or delayed release of the active compound (s) contained therein.

According to one embodiment, the pharmaceutical composition of the invention is in an adapted form for an oral administration. Forms adapted to oral administration may be solid, semi-solid or liquid. Some preferred, but non-limiting examples of such forms include liquid, paste or solid compositions, and more particularly films, tablets, tablets formulated for extended or sustained release, capsules (including soft and hard gelatin capsules), pills, dragees, lozenges, sachets, cachets, powder, liquids, gels, syrups, slurries, elixirs, emulsions, solutions, and suspensions.

In one embodiment, the pharmaceutical composition of the invention is in a form designed for film drug delivery. In one embodiment, the pharmaceutical composition of the invention is in the form of a film. In one embodiment, the film is a thin-film, a dissolving film, an oral drug strip, a biological film, and/or a 3D printed film. In one embodiment, film form of the pharmaceutical composition of the invention is designed for oral administration.

According to another embodiment, the pharmaceutical composition of the invention is in an adapted form for an injection, especially to be injected to the subject by intravenous, intramuscular, intraperitoneal, intrapleural, subcutaneous, transdermal injection or infusion.

According to another embodiment, the pharmaceutical composition of the invention is in an adapted form for a topical administration. Examples of forms adapted for topical administration include, without being limited to, liquid, paste or solid compositions, and more particularly aqueous solutions, drops, dispersions, sprays, ointments, cremes, lotions, microcapsules, micro- or nanoparticles, polymeric patch, or controlled-release patch, and the like.

According to another embodiment, the pharmaceutical composition of the invention is in an adapted form for a rectal administration. Examples of forms adapted for rectal administration include, without being limited to, suppository, micro enemas, enemas, gel, rectal foam, cream, ointment, and the like.

According to another embodiment, the pharmaceutical composition of the invention is in an adapted form for an administration by inhalation. Examples of forms adapted for administration by inhalation include, without being limited to aerosols.

The pharmaceutical preparations of the invention are preferably in a unit dosage form, and may be suitably packaged, for example in a box, blister, vial, bottle, sachet, ampoule or in any other suitable single-dose or multi-dose holder or container (which may be properly labeled); optionally with one or more leaflets containing product information and/or instructions for use.

All references to compounds of Formula (I) or (II) include references to salts, solvates, multi-component complexes and liquid crystals thereof. All references to compounds of Formula (I) or (II) include references to polymorphs and crystal habits thereof. All references to compounds of Formula (I) or (II) include references to pharmaceutically acceptable prodrugs and prodrugs thereof.

The compounds of Formula (I) or (II) and subformulae thereof contain at least one asymmetric centre(s) and thus may exist as different stereoisomeric forms. Accordingly, all references to compounds of Formula (I) or (II) include references to all possible stereoisomers and includes not only the racemic compounds but the individual enantiomers and their non-racemic mixtures as well. When a compound is desired as a single enantiomer, such single enantiomer may be obtained by stereospecific synthesis, by resolution of the final product or any convenient intermediate, or by chiral chromatographic methods as each are known in the art. Resolution of the final product, an intermediate, or a starting material may be carried out by any suitable method known in the art. Bonds from an asymmetric carbon in compounds are generally depicted using a solid line (——), a solid wedge (◀), or a dotted wedge (''''''llll). The use of either a solid or dotted wedge to depict bonds from an asymmetric carbon atom is meant to indicate that only the stereoisomer shown is meant to be included.

All references to compounds of Formula (I) or (II) include references to isotopically-labelled compounds of Formula (I) or (II), including deuterated compounds of Formula (I) or (II).

The compounds of the invention may be in the form of pharmaceutically acceptable salts. Pharmaceutically acceptable salts of the compounds of Formula (I) or (II) include the acid addition and base salts thereof.

- Suitable acid addition salts are formed from acids which form non-toxic salts. Examples include the acetate, adipate, aspartate, benzoate, besylate, bicarbonate/carbonate, bisulphate/sulphate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate and xinofoate salts.
- Suitable base salts are formed from bases which form non-toxic salts. Examples include the aluminium, arginine, benzathine, calcium, choline, diethylamine, 2-(diethylamino)ethanol, diolamine, ethanolamine, glycine, 4-(2-hydroxyethyl)-morpholine, lysine, magnesium, meglumine, morpholine, olamine, potassium, sodium, tromethamine and zinc salts.
- Hemisalts of acids and bases may also be formed, for example, hemisulphate and hemicalcium salts.
- Preferred pharmaceutically acceptable salts include hydrochloride/chloride, hydrobromide/bromide, bisulphate/sulphate, nitrate, citrate and acetate.
- When the compounds of Formula (I) or (II) contain an acidic group as well as a basic group the compounds of the invention may also form internal salts, and such compounds are within the scope of the invention. When the compounds of the invention contain a hydrogen-donating heteroatom (e.g., NH), the invention also covers salts and/or isomers formed by transfer of said hydrogen atom to a basic group or atom within the molecule.

Pharmaceutically acceptable salts of compounds of Formula (I) or (II) may be prepared by one or more of these methods:

- (i) by reacting the compound of Formula (I) or (II) with the desired acid;
- (ii) by reacting the compound of Formula (I) or (II) with the desired base;
- (iii) by removing an acid- or base-labile protecting group from a suitable precursor of the compound of Formula (I) or (II) or by ring-opening a suitable cyclic precursor, e.g., a lactone or lactam, using the desired acid; and/or
- (iv) by converting one salt of the compound of Formula (I) or (II) to another by reaction with an appropriate acid or by means of a suitable ion exchange column.
- All these reactions are typically carried out in solution. The salt may precipitate from solution and be collected by filtration or may be recovered by evaporation of the solvent. The degree of ionization in the salt may vary from completely ionized to almost non-ionized.

The pharmaceutical composition of the invention may be manufactured by methods well known by one skilled in the art.

The compounds of formula (I) or (II) may be commercially purchased and/or manufactured by standard synthetic procedures and extraction and/or purification methods commonly used in the field of organic synthetic chemistry, which are well-known by one skilled in the art.

The invention also relates to a pharmaceutical composition according to the invention as described hereinabove for use as a medicament. The invention further relates to the use of a compound of formula (I) according to the invention as described hereinabove for the preparation or the manufacture of a medicament.

According to one embodiment, the pharmaceutical composition is for use in the treatment and/or prevention of a brain disorder. In one embodiment, the brain disorder is a disorder of the central nervous system (CNS). In one embodiment, the pharmaceutical composition is for use in the treatment and/or prevention of a disorder of the central nervous system or of its function.

In some embodiments, the brain disorders comprise motor disorders, mood disorders, neurological disorders and neurodegenerative disorders. In some embodiments, the brain disorder may be the consequence of a neurotransmission disorder. In some embodiments, the brain disorder may be characterized by a pathological dysregulated synaptic activity or neurodegenerative processes. According to one embodiment, the pharmaceutical composition is for use in the treatment and/or prevention of a disorder characterized by a pathological dysregulated synaptic activity or neurodegenerative processes.

In some other embodiments, the brain disorder may be the consequence of the action of a pathogenic factor or agent. According to one embodiment, pathogenic factors or agents may be bacteria, viruses, fungus or parasites. According to another embodiment, pathogenic factors or agents may also be addictive substances such as alcohol or drugs. Still according to another embodiment, pathogenic factors or agents may further be any molecule or substance which causes an inflammation, in particular a neuroinflammation, whether external to the body or produced/secreted by the body.

In one embodiment, the bacterium may be *Neisseria meningitidis, Streptococcus pneumoniae, Haemophilus influenzae, Listeria monocytogenes, Escherichia coli*, or *Streptococcus agalactiae.*

In one embodiment, the virus may be an enterovirus, a poliovirus, Epstein-Barr virus, a herpes virus, a cytomegalovirus, measles, Human immunodeficiency virus (HIV), SARS-Cov-2 and its variants, or Zika virus.

In one embodiment, the parasite may be *Toxoplasma gondii.*

In one embodiment, the molecule or substance which causes an inflammation may be $H^+$ ions, radical oxygen species (ROS), amyloid.

In some embodiments, a disorder of the central nervous system may encompass a motor disorder, a mood disorder, a neurological disorder or a neurodegenerative disorder. In some embodiments, the disorder of the central nervous system may be the consequence of a neurotransmission disorder. In some other embodiments, the disorder of the central nervous system may be the consequence of the action of a pathogenic factor or agent.

According to one embodiment, the pharmaceutical composition is for use in the treatment and/or prevention of a neurotransmission disorder. According to the present invention, a "neurotransmission disorder" means a disorder associated with or due to alteration in the neurotransmission system/pathway, disturbances/dysfunction of neurotransmitter metabolism. The term "neurotransmission disorder" may be used interchangeably with the term "neurotransmitter disorder".

In one embodiment, the neurotransmission disorder is a disorder associated with an altered adrenergic, dopaminergic, GABAergic, glutamatergic, noradrenergic and/or serotoninergic neurotransmission. Within the scope of the invention the term "altered" encompasses both a hyperactivity or a hypoactivity of the neurotransmitter as compared to reference activity level. In one embodiment, the neurotransmission disorder is a disorder associated with a hyperactivity of the adrenergic, dopaminergic, GABAergic, glutamatergic, noradrenergic and/or serotoninergic neurotransmitter.

As used herein, hyperactivity or hypoactivity may be assessed by a change of at least 10% of the level of the neurotransmitter activity as compared to a reference level. Within the scope of the instant invention, the terms "at least 10%" encompasses 10%, 15%, 20%, 25%, 30%, 35%, 40%, 45%, 50%, 55%, 60%, 65%, 70%, 75%, 80%, 85%, 90%, 95%, 100%, 125%, 150%, 175%, 200%, 225%, 250%, 275%, 300%, 350%, 400%, 450%, 500%, 550%, 600%, 650%, 700%, 750%, 800%, 850%, 900%, 950%, 1,000% and above.

The level of neurotransmitters may be assessed according to any acknowledged method from the state of the art. The level of neurotransmitters may be assessed from a saliva, blood or urine sample, in practice with commercial kits. Alternatively, biosensors may be employed.

In one embodiment, a neurotransmission disorder may be a motor disorder, a mood disorder, a neurological disorder, a neurodegenerative disorder or an inflammatory disorder due to a pathogenic factor or agent.

According to one embodiment, the pharmaceutical composition is for use in the treatment and/or prevention of a motor disorder.

In one embodiment, the motor disorder is selected from the group comprising or consisting of Parkinson's disease, Huntington disease, muscular disorders, multiple system atrophy, genetic and non-genetic dystonia including functional dystonia, restless legs syndrome, cerebellar disorders, and medication-induced motor disorder.

In a particular embodiment, the motor disorder is Parkinson's disease. According to the present invention, the term "Parkinson's disease" includes, but is not limited to, genetic and idiopathic (or non-genetic) Parkinson's disease.

In some embodiment, the motor disorder is a medication-induced motor disorder. In other words, a medication-induced motor disorder is a disorder induced by the treatment of a motor disorder, such as for example a disorder induced by a treatment for Parkinson's disease. In still other words, a medication-induced motor disorder is an adverse side effect of the treatment of a motor disorder. In a particular embodiment, the medication-induced motor disorder is an adverse side effect of a treatment for Parkinson's disease.

In a particular embodiment, the pharmaceutical composition is for use in the treatment and/or prevention of the side effects produced by a medication used to treat a motor disorder. According to the present invention, the term "side effects produced by another medication" refers, but is not limited to, side effects produced by or appeared during the treatment with, such as for example, dopamine agonist, dopamine partial agonist, L-DOPA, MAO inhibitors and the like.

In a particular embodiment, cerebellar disorders include, but are not limited to, ataxia.

According to another embodiment, the pharmaceutical composition is for use in the treatment and/or prevention of a mood disorder.

In one embodiment, the mood disorder is selected from the group comprising or consisting of psychotic disorders, schizophrenia, psychosis, bipolar disorder, bipolar depression, depression, anxiety, panic disorders, Tourette syndrome, obsessive compulsive disorders, and attention deficits disorders including attention deficit hyperactive disorders.

In a particular embodiment, the mood disorder is anxiety.

According to one embodiment, the pharmaceutical composition is for use in the treatment and/or prevention of a neurological disorder.

In one embodiment, the neurological disorder is selected from the group comprising or consisting of Epilepsy, Alzheimer's Disease (AD), Mild Cognitive Impairment (MCI), Attention-Deficit Hyperactivity Disorder (ADHD), or Hyper-kinetic Disorder, agnosia, Amyotrophic Lateral Sclerosis (ALS), ataxia including Friedreich's ataxia, Canavan disease, dementia, neuralgia, migraine, headaches, and tension headaches.

In a particular embodiment, the neurological disorder is epilepsy. According to the present invention, the term "epilepsy" includes, but is not limited to, refractory epilepsy, genetic epilepsy, epileptic disorders, child/infant epilepsy such as Dravet syndrome, diseases characterized by recurrent seizures or epileptic episodes. In one embodiment, the diseases characterized by recurrent seizures or epileptic episodes comprise or consist of injury-induced epilepsy, to stroke-induced epilepsy, brain trauma-induced epilepsy and tumor-induced epilepsy.

According to one embodiment, the pharmaceutical composition is for use in the treatment and/or prevention of a neurodegenerative disorder.

In one embodiment, the neurodegenerative disorder is selected from Alzheimer's disease, Amyotrophic lateral sclerosis, Friedreich's ataxia, Huntington's disease, Lewy body disease, Parkinson's disease, Spinal muscular atrophy.

In a particular embodiment, the neurodegenerative disease is Alzheimer's disease.

According to one embodiment, the pharmaceutical composition is for use in the treatment and/or prevention of an inflammatory disorder due to a pathogenic factor or agent.

In one embodiment, the inflammatory disorder due to a pathogenic factor or agent is a chronic inflammation.

In one embodiment, the inflammatory disorder due to a pathogenic factor or agent is selected from encephalitis, myelitis, meningitis, grey-matter atrophy, encephalopathy, HIV-induced neurological disorder, SARS-CoV-2-induced neurological disorder, neuronal destruction, infection or damage of oligodendrocytes, infection or damage of astrocytes, infection or damage of neurons, and apoptotic neurons.

In one embodiment, the inflammatory disorder due to a pathogenic factor or agent is selected from encephalitis, myelitis, meningitis, grey-matter atrophy, encephalopathy, HIV-induced neurological disorder, SARS-CoV-2-induced neurological disorder, and infection or damage of oligodendrocytes.

According to another embodiment, the pharmaceutical composition is co-administered with another therapeutic agent as described herein above. In one embodiment, said another therapeutic agent is administered in the same pharmaceutical composition. In another embodiment, said another therapeutic agent is administered in another pharmaceutical composition.

According to an embodiment, the pharmaceutical composition further comprises another therapeutic agent. In one embodiment, said therapeutic agent is a therapeutic agent for treating and/or preventing a brain disorder, preferably a CNS disorder. In one embodiment, said therapeutic agent is a therapeutic agent for treating and/or preventing a motor disorder, a mood disorder, a neurological disorder or a neurodegenerative disorder. In one embodiment, said therapeutic agent is a dopamine agonist, an inhibitor of the precursor of dopamine (or inhibitor of L-DOPA) or a monoamine oxidase inhibitor (or a MAO inhibitor), and the like.

The invention thus also relates to methods of treatment and/or prevention of disorders, comprising the administration of a therapeutically effective amount of a pharmaceutical composition according to the invention, as described hereinabove, to a subject in need thereof. The invention thus also relates to the use of a pharmaceutical composition according to the invention, as described hereinabove, in the manufacture of a medicament.

Another object of the invention is a method of treating a subject in need thereof comprising the administration of a therapeutically effective amount of a pharmaceutical composition according to the invention, as described hereinabove.

In one embodiment, the method of the invention further comprises the administration of another therapeutic agent, such as for example a dopamine agonist, an inhibitor of the precursor of dopamine (or inhibitor of L-DOPA) or a monoamine oxidase inhibitor (or a MAO inhibitor). In some embodiments, said another therapeutic agent may be administered before, during or after the administration of the pharmaceutical composition according to the invention. In some embodiments, administration of said another therapeutic agent may be sequential or simultaneous to the administration of the pharmaceutical composition according to the invention.

According to one embodiment, the subject is suffering from a neurological or neurodegenerative disorder. In one embodiment, the subject is at risk of developing a neurological or neurodegenerative disorder. According to one embodiment, the subject is suffering from a disorder induced by a pathogenic factor or agent, preferably an inflammatory disorder induced by a pathogenic factor or agent.

The present invention also relates to a method for improving cognition and/or memory of a subject, comprising the administration to the subject of a therapeutically effective amount of a pharmaceutical composition according to the invention, as described hereinabove. Still another object of the present invention is a method for restoring neurotransmission of a subject, comprising the administration to the subject of a therapeutically effective amount of a pharmaceutical composition according to the invention, as described hereinabove.

In certain embodiments, the therapeutically effective amount to be administered may depend upon a variety of parameters, including the material selected for administration, whether the administration is in single or multiple doses, and the individual's parameters including age, physical condition, size, weight, and the severity of the disorder.

In certain embodiments, an effective amount of the active agent, i.e. the compound of formula (I), may comprise from about 0.001 mg to about 3,000 mg, per dosage unit, preferably from about 0.05 mg to about 100 mg, per dosage unit.

Within the scope of the instant invention, from about 0.001 mg to about 3,000 mg includes, from about 0.001 mg, 0.002 mg, 0.003 mg, 0.004 mg, 0.005 mg, 0.006 mg, 0.007 mg, 0.008 mg, 0.009 mg, 0.01 mg, 0.02 mg, 0.03 mg, 0.04 mg, 0.05 mg, 0.06 mg, 0.07 mg, 0.08 mg, 0.09 mg, 0.1 mg, 0.2 mg, 0.3 mg, 0.4 mg, 0.5 mg, 0.6 mg, 0.7 mg, 0.8 mg, 0.9 mg, 1 mg, 2 mg, 3 mg, 4 mg, 5 mg, 6 mg, 7 mg, 8 mg, 9 mg, 10 mg, 20 mg, 30 mg, 40 mg, 50 mg, 60 mg, 70 mg, 80 mg, 90 mg, 100 mg, 150 mg, 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 950 mg, 1,000 mg, 1,100 mg, 1,150 mg, 1,200 mg, 1,250 mg, 1,300 mg, 1,350 mg, 1,400 mg, 1,450 mg, 1,500 mg, 1,550 mg, 1,600 mg, 1,650 mg, 1,700 mg, 1,750 mg, 1,800 mg, 1,850 mg, 1,900 mg, 1,950 mg, 2,000 mg, 2,100 mg, 2,150 mg, 2,200 mg, 2,250 mg, 2,300 mg, 2,350 mg, 2,400 mg, 2,450 mg, 2,500 mg, 2,550 mg, 2,600 mg, 2,650 mg, 2,700 mg, 2,750 mg, 2,800 mg, 2,850 mg, 2,900 mg, 2,950 mg and 3,000 mg, per dosage unit.

In certain embodiments, the active agent, i.e. the compound of formula (I), may be at dosage levels sufficient to deliver from about 0.001 mg/kg to about 100 mg/kg, from about 0.01 mg/kg to about 50 mg/kg, preferably from about 0.1 mg/kg to about 40 mg/kg, preferably from about 0.5 mg/kg to about 30 mg/kg, from about 0.01 mg/kg to about 10 mg/kg, from about 0.1 mg/kg to about 10 mg/kg, and more preferably from about 1 mg/kg to about 25 mg/kg, of subject body weight per day.

In certain embodiments, each dosage unit may be administered three times a day, two times a day, once a day, every other day, every three days, every week, every two weeks, every three weeks, or every four weeks.

In certain embodiments, the therapeutic treatment encompasses an administration of a plurality of dosage units, including two, three, four, five, six, seven, eight, nine, ten, eleven, twelve, thirteen, fourteen, or more administrations.

The present invention further relates to a kit of parts comprising the pharmaceutical composition of the invention, and optionally means to administer said pharmaceutical composition to a subject in need thereof. In one embodiment, the kit of parts of the invention further comprises another pharmaceutical composition comprising another therapeutic agent, and optionally means to administer said another pharmaceutical composition.

EXAMPLES

The present invention is further illustrated by the following examples.

Example 1: Cmpd1 in a Model of Epileptic Activity

Methods

Compound was tested in zebrafish paradigms reaction to environmental stimuli, epileptic activity and dopaminergic hyperactivity. Zebrafish used in present studies were raised in regular conditions of housing in tanks of appropriate size and circadian rhythm (12:12 photoperiod, light/darkness). The aqueous medium used for the maintenance and experimental conditions was Instant Ocean®. The water maintained between at 27° C. or 29° C., pH between 7.2-7.5 and a conductivity value between 480-520 μS. Zebrafish embryos were placed in sterile petri dishes before being transferred to plates after the hatching.

For experimental studies, larvae of up to 5 dpf were placed in flat bottom 96-well plates. At the treatment time, the medium was replaced by 150 μL fresh medium. Pentetrazole (PTZ) and/or Cmpd1 (treatment), or vehicle (control) were added (up to 210-240 μL) to the wells followed by video recording.

Figure 7:
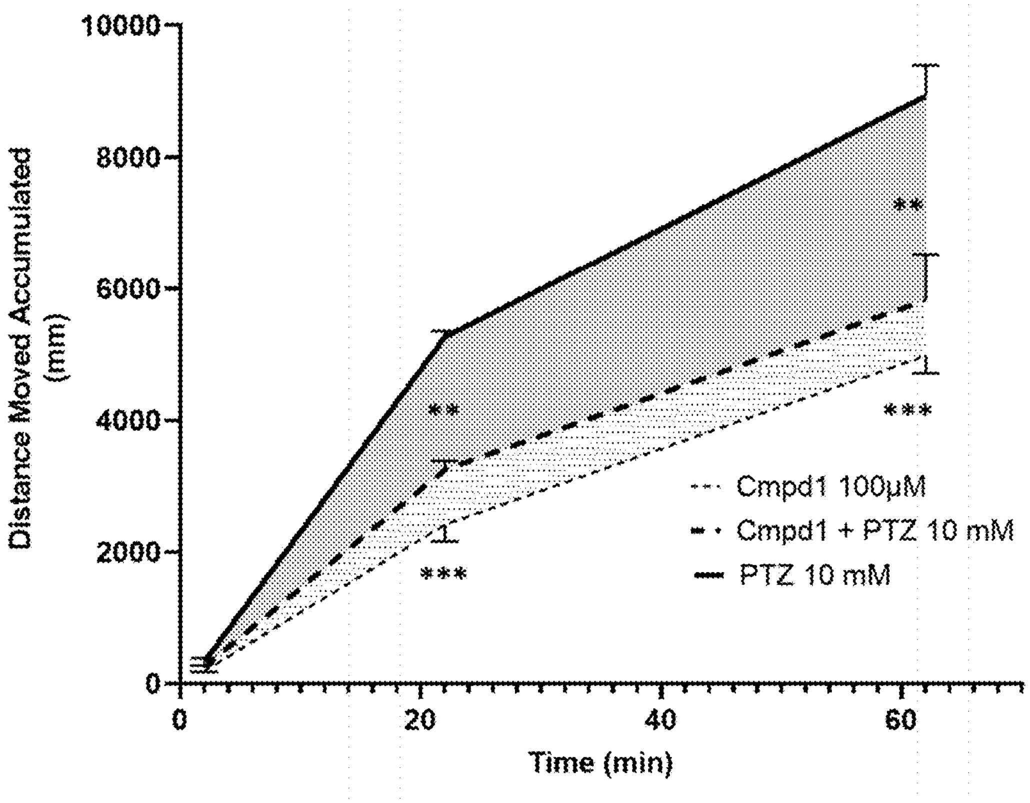
FIG. 7 is a graph showing distance moved accumulated at 2 min, 4 min, 10 min, and 20 min by zebra fish larvae treated with pentetrazole at a concentration of 10 mM (solid line) or co-treated with pentetrazole at a concentration of 10 mM and Cmpd1 at a concentration of 100 μM (dotted line) or with Cmpd1 at a concentration of 100 μM (dotted thin line). The areas of response to pentetrazole versus to treatment with Cmpd1 alone or in combination with pentetrazole are represented by connecting lines and pattern backgrounds. One-way anova with Tukey for multiple comparisons, Cmpd1+PTZ vs PTZ$P<0.002$; Cmpd1 vs PTZ*$P<0.0001$.
Figure 8:
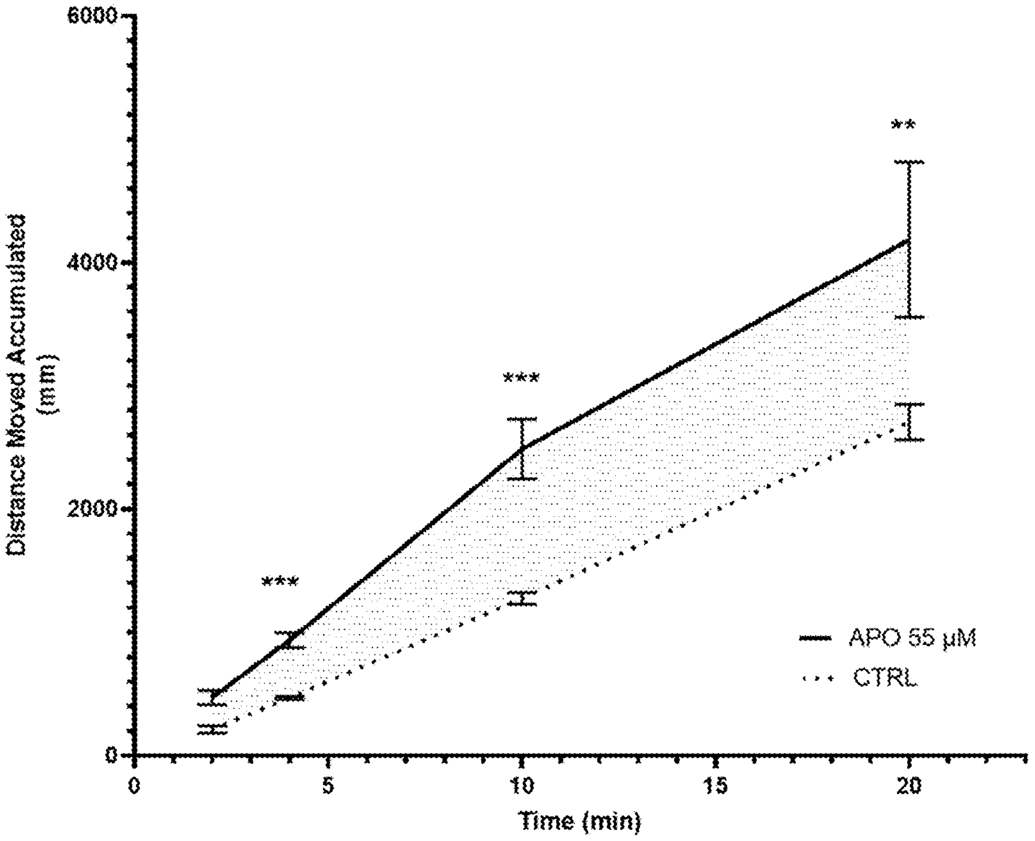
FIG. 8 is a graph showing distance moved accumulated at 2 min, 4 min, 10 min and 20 min by zebra fish larvae treated with a vehicle (CTRL, solid lines), apomorphine at a concentration of 55 μM (thin line). The area of response to apomorphine versus control is represented by connecting lines. One-way anova with Tukey for multiple comparisons, CTRL vs APO*$P<0.0003$; $P<0.022$.

Locomotion of larvae was recorded using Noldus daniovisio system equipped with infrared light detection. Ethovision XT15 software controlled the temperature of plate (28° C.) and chamber light conditions. The experimental recording was done with a cycle of light period (20 min) followed by dark period (45 min). After recording data were analysed using Ethovision XT15 software package. The distance moved by larvae was calculated for each period of 2 min recording (FIGS. 1 to 6 and 10) or as accumulated value of distance at 2 min (initiation), at 4 min at 10 min and at 20 min (switch to darkness) or at 60 min (end of recording) (FIGS. 7 and 8).

All compounds were dissolved in medium or medium containing DMSO at indicated concentrations.

Results

Larvae treated with vehicle show a normal locomotor (FIGS. 1 and 5) with an increase of their activity after switch to dark condition, peaking after the minute 20 and decreasing afterwards till reach normal locomotion levels about the end of the recording.

Figure 2:
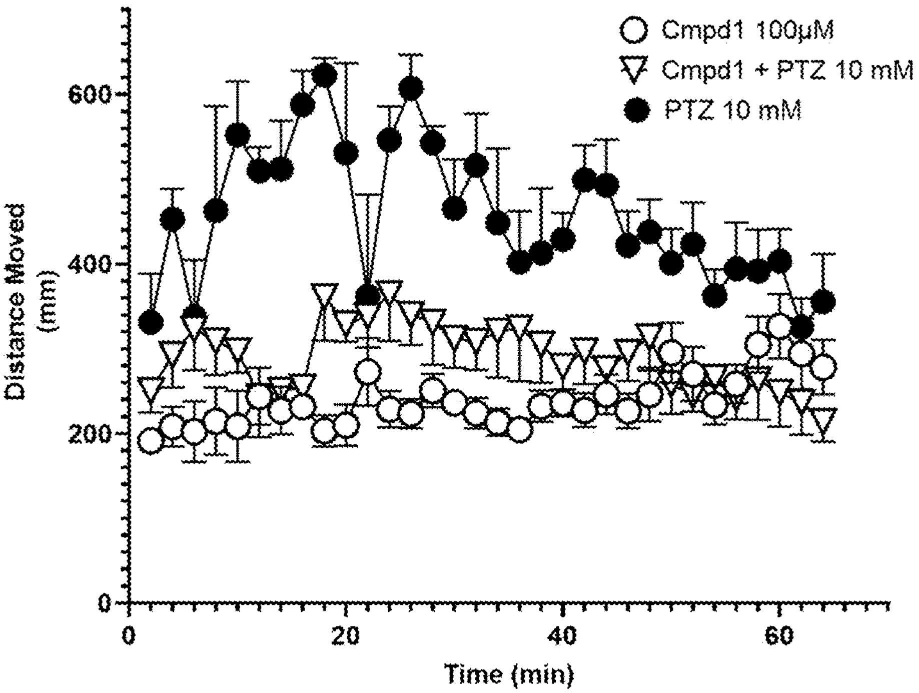
FIG. 2 is a graph showing distance moved by zebra fish larvae treated with pentetrazole at a concentration of 10 mM (black circles) or co-treated with pentetrazole at a concentration of 10 mM and Cmpd1 at a concentration of 100 μM (inverted white triangles) or with Cmpd1 at a concentration of 100 μM (open circles).
Figure 6:
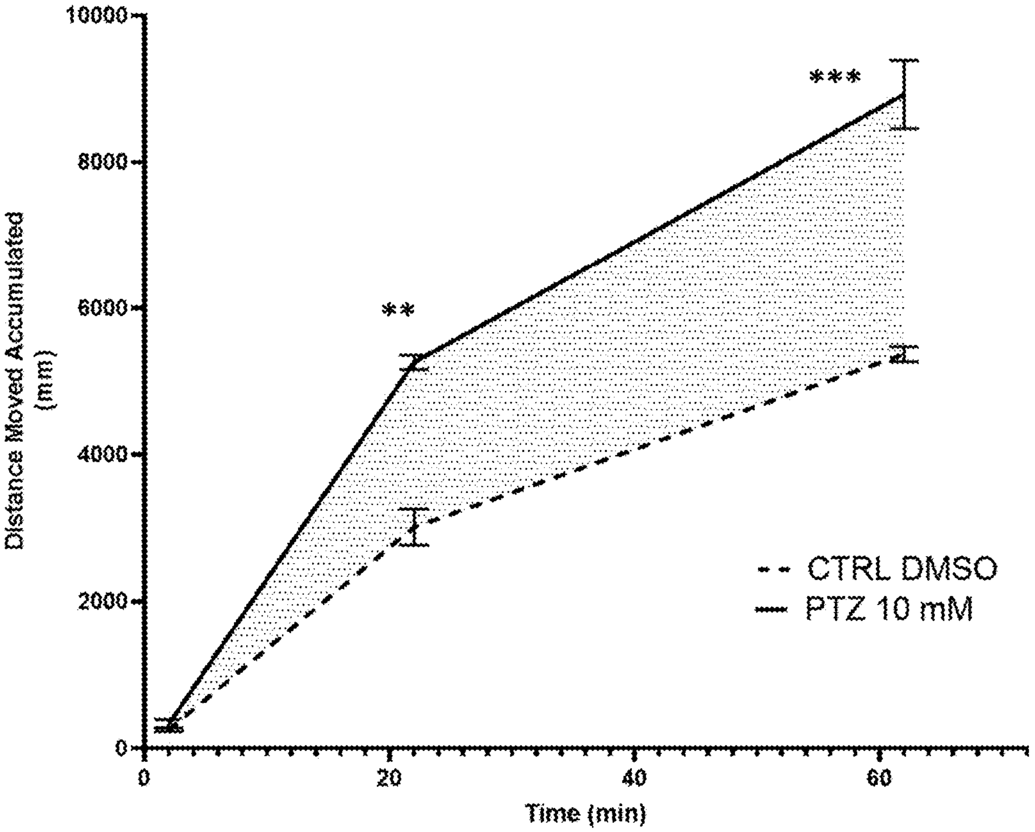
FIG. 6 is a graph showing distance moved accumulated at 2 min, 22 min and 60 min by zebra fish larvae treated with a vehicle (CTRL, dotted line), pentetrazole at a concentration of 10 mM (solid line). The area of response to pentetrazole versus control is represented by connecting lines and pattern background. One-way anova with Tukey for multiple comparisons, CTRL vs PTZ*$P<0.001$, $P<0.003$.

Treatment of zebra fish larvae with pentetrazole, a pro-epileptic/seizure-inducing compound, induces a clear increase of locomotor activity in both light and dark conditions (FIGS. 1 and 2, black circles, and FIG. 6). This increase is associated to the seizure induced activity. Co-treatment with Cmpd1 at a concentration of 100 μM and pentetrazole at a concentration of 10 mM induced a decrease of the locomotor activity of ZF larvae induced by Pentetrazole alone (FIG. 2, inverted triangles, and FIG. 7). Cmpd1 stabilizes locomotion to levels close to normal locomotion observed in vehicle treated zebra fishes (FIG. 2, open circles, and FIG. 7).

These results thus show that Cmpd1 has an anti-epileptic activity.

Example 2: Cmpd1 in a Model of Hyperdopaminergic Activity

Methods

The same methods as disclosed in Example 1 ware carried out for Example 2, except that the pentetrazole was replaced by apomorphine (APO).

Results

Figure 3:
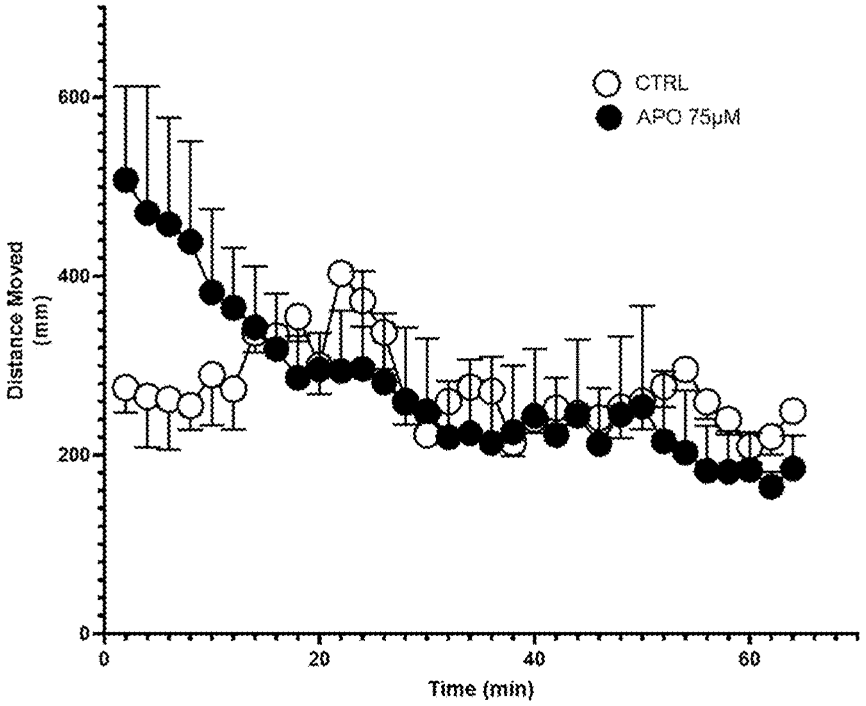
FIG. 3 is a graph showing distance moved by zebra fish larvae treated with a vehicle (CTRL, open circles), apomorphine at a concentration of 75 μM (black circles)
Figure 4:
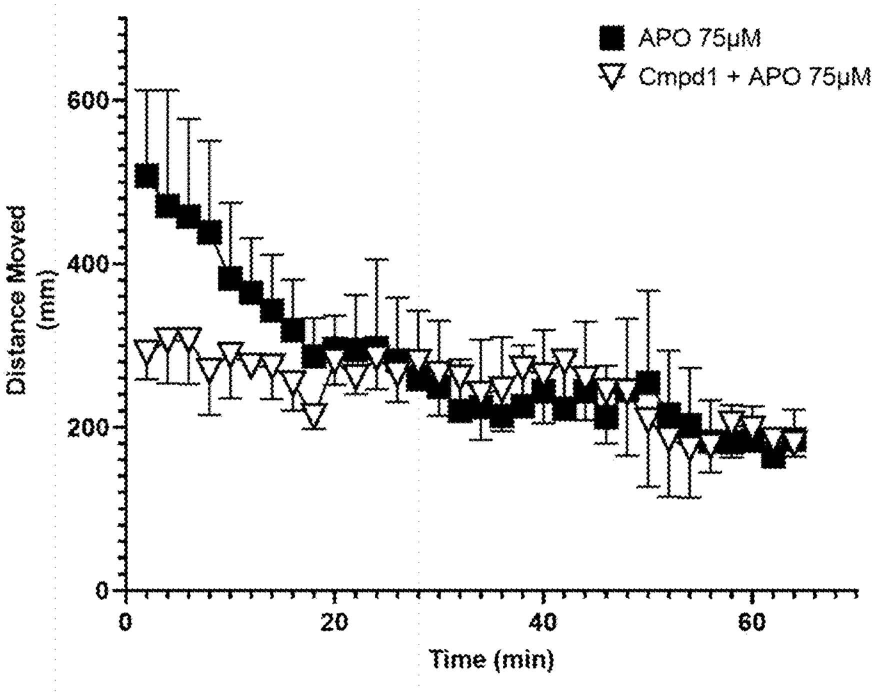
FIG. 4 is a graph showing distance moved by zebra fish larvae treated with apomorphine at a concentration of 75 μM (black circles) or co-treated with apomorphine at a concentration of 75 μM and Cmpd1 at a concentration of 100 μM (inverted white triangles).

Treatment of zebra fish larvae with apomorphine a dopamine agonist induces a clear increase of locomotor activity in light conditions (FIG. 3, black circles, and FIG. 8). This increase is associated to the hyperactivity of the dopaminergic neurotransmission pathways leading to motor hyperactivity.

Co-treatment with Cmpd1 at a concentration of 100 μM and apomorphine at a concentration of 75 μM (FIG. 4, inverted triangles), or 55 μM (FIG. 9) induced a decrease of the locomotor activity of zebra fish larvae induced by apomorphine alone.

Figure 5:
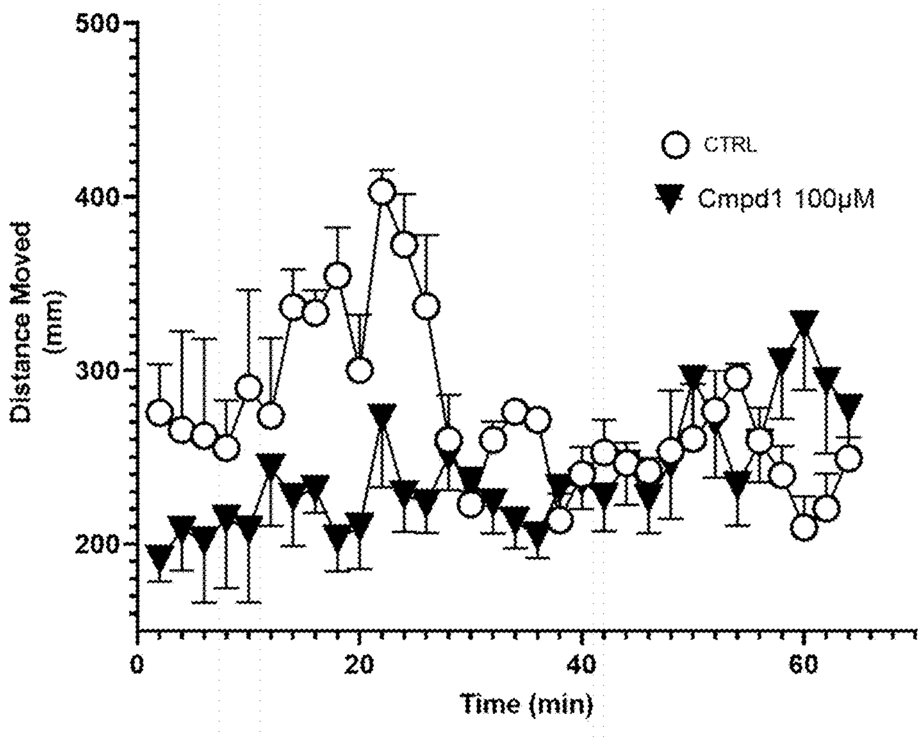
FIG. 5 is a graph showing distance moved by zebra fish larvae treated with vehicle (CTRL, open circles) or Cmpd1 at a concentration of 100 μM (inverted black triangles).
Figure 9:
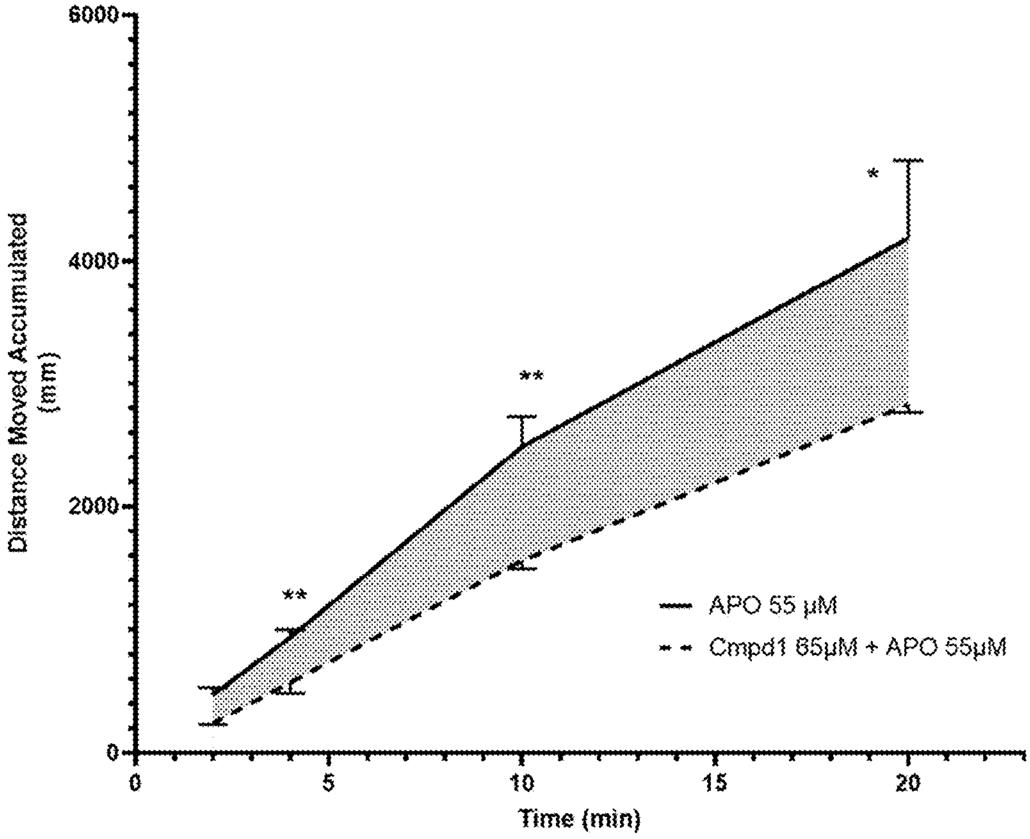
FIG. 9 is a graph showing distance moved accumulated at 2 min, 22 min and 60 min by zebra fish larvae treated with apomorphine at a concentration of 55 μM (solid line) or co-treated with apomorphine at a concentration of 55 μM and Cmpd1 at a concentration of 65 μM (dotted line). The area of response to apomorphine versus to treatment with Cmpd1 in combination with apomorphine is represented by connecting lines and pattern background. One-way anova with Tukey for multiple comparisons, Cmpd1+APO vs APO**$P<0.0046$; Cmpd1 vs APO*$P<0.06$.
Figure 10:
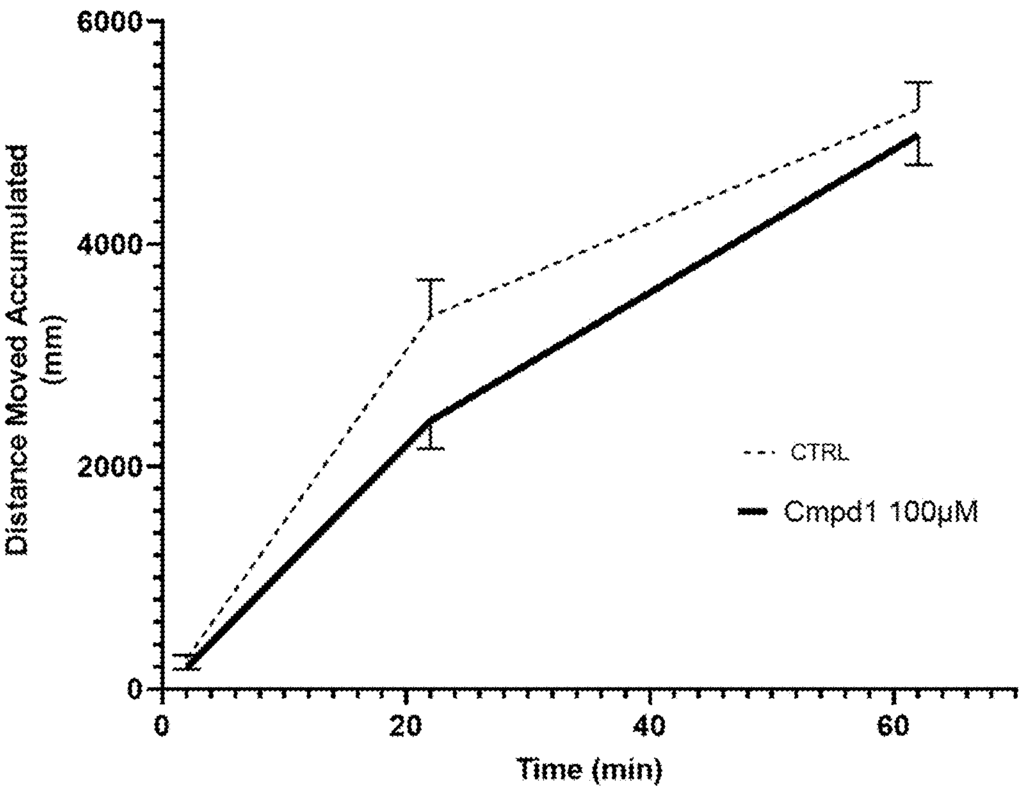
FIG. 10 is a graph showing distance moved accumulated at 2 min, 22 min and 60 min by zebra fish larvae treated with vehicle (CTRL, dotted line) or Cmpd1 at a concentration of 100 μM (solid line). The area of response to vehicle treatment versus to treatment with Cmpd1 is represented by connecting lines.

Cmpd1 stabilizes locomotion to levels close to normal locomotion observed in vehicle treated zebra fish (FIG. 5, black inverted triangles, and FIGS. 9 and 10). Cmpd1 reduces apomorphine-induced locomotion activity strongly during the first period of the assay (up to ~20 min, FIG. 9). Cmpd1 alone maintains a low level of locomotion activity suppressing also the peak due to change to dark condition (FIGS. 5 and 10).

Therefore, it has been demonstrated that Cmpd1 is a stabilizer of the hyperdopaminergic activity. Suppressive effect on the change light-to-dark indicates also an effect of Cmpd1 on the stress-mood disturbance induced by a challenging environment. These results suggest that the compound may be used to treat motor disorders and mood disorders.

The invention claimed is:

1. A method of treating a central nervous system disorder in a subject in need thereof comprising a step of administration of a therapeutically effective amount of a pharmaceutical composition to said subject;

wherein the pharmaceutical composition comprises a compound of formula (II)

(II)

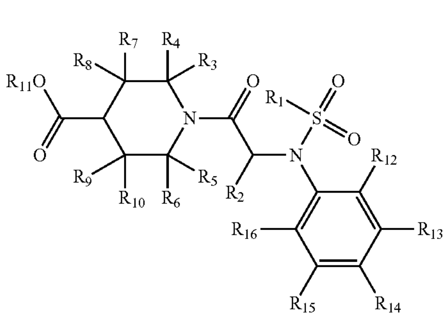

or a pharmaceutically acceptable salt and/or solvate thereof, wherein:

$R_1$, $R_2$ and $R_{11}$ are each independently $C_1$-$C_3$ alkyl, $R_3$, $R_4$, $R_5$, $R_6$, $R_7$, $R_8$, $R_9$ and $R_{10}$ are each independently selected from hydrogen, halogen, hydroxyl, —$NH_3$, —$NO_3$, —SH, $C_1$-$C_3$ alkyl, $C_1$-$C_3$ haloalkyl, $C_1$-$C_3$ alkoxy, and $C_1$-$C_3$ thioalkyl, $R_{12}$, $R_{13}$, $R_{15}$ and $R_{16}$ are each independently selected from hydrogen, halogen, hydroxyl, —$NH_3$, —$NO_3$, —SH, $C_1$-$C_3$ alkyl, $C_1$-$C_3$ haloalkyl, $C_1$-$C_3$ alkoxy, and $C_1$-$C_3$ thioalkyl, and $R_{14}$ is $C_1$-$C_3$ alkyl, and at least one pharmaceutically acceptable excipient;

wherein the central nervous system disorder comprises a neurological disorder selected from the group consisting of Epilepsy, Alzheimer's Disease (AD), Mild Cognitive Impairment (MCI), Attention-Deficit Hyperactivity Disorder (ADHD), Hyper-kinetic Disorder, agnosia, Amyotrophic Lateral Sclerosis (ALS), Huntington's disease, Lewy body disease, Parkinson's disease, Spinal muscular atrophy, ataxia, Canavan disease, dementia, neuralgia, migraine, headaches, and tension headaches.

2. The method according to claim 1, wherein $R_1$ is a methyl group, $R_2$ is a methyl group, and/or $R_{11}$ is an ethyl group.

3. The method according to claim 1, wherein:

$R_3$, $R_4$, $R_5$, $R_6$, $R_7$, $R_8$, $R_9$ and $R_{10}$ are each independently selected from hydrogen and $C_1$-$C_3$ alkyl, and $R_{12}$, $R_{13}$, $R_{15}$ and $R_{16}$ are each independently selected from hydrogen and $C_1$-$C_3$ alkyl.

4. The method according to claim 1, wherein the compound of formula (II) is compound (1)

(1)

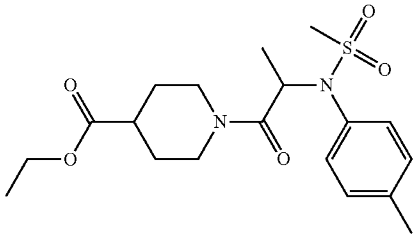

or a pharmaceutically acceptable salt and/or solvate thereof.

5. The method according to claim 1, wherein the neurological disorder is epilepsy.

6. The method according to claim 1, wherein the neurodegenerative disorder is selected from Alzheimer's disease, Amyotrophic lateral sclerosis, Friedreich's ataxia, Huntington's disease, Lewy body disease, Parkinson's disease, and Spinal muscular atrophy.

7. The method according to claim 1, wherein the neurodegenerative disorder is Alzheimer's disease.

8. The method according to claim 1, wherein the method further comprises a step of administration of another therapeutic agent for the treatment said central nervous system disorder.

9. The method according to claim 1, wherein the administration is oral administration.

10. The method according to claim 1, wherein the pharmaceutical composition is in the form of a film.

* * * * *